United States Patent
Guerrero et al.

[19]

[11] Patent Number: 5,885,290
[45] Date of Patent: Mar. 23, 1999

[54] INTRA-ORAL BONE DISTRACTION DEVICE

[76] Inventors: Cesar A. Guerrero, Calle Roraima, Quinta Montalban, Valle Arriba, Caracas 1060, Venezuela; William H. Bell, 5705 Bent Creek Trail, Dallas, Tex. 75252

[21] Appl. No.: 820,612

[22] Filed: Mar. 19, 1997

Related U.S. Application Data

[60] Provisional application No. 60/033,287 Dec. 9, 1996.

[51] Int. Cl.⁶ .................................................. A61B 17/68
[52] U.S. Cl. .............................. 606/71; 606/60; 606/73; 433/7
[58] Field of Search .................................. 606/53, 60, 69, 606/70, 71, 105, 54, 55, 57, 73; 433/7; 29/896.1, 896.11

[56] References Cited

U.S. PATENT DOCUMENTS

| | | | |
|---|---|---|---|
| 3,284,902 | 11/1966 | Dillberg et al. | 32/14 |
| 3,921,294 | 11/1975 | Wallshein | 32/14 |
| 3,977,082 | 8/1976 | Siatkowski | 32/14 |
| 4,026,023 | 5/1977 | Fisher | 32/14 |
| 4,144,643 | 3/1979 | Krygier | 32/14 |
| 4,197,644 | 4/1980 | Ackerman, Jr. | 433/7 |
| 4,482,318 | 11/1984 | Förster | 433/7 |
| 4,483,674 | 11/1984 | Schütz | 433/22 |
| 4,571,177 | 2/1986 | Dahan | 433/7 |
| 4,573,914 | 3/1986 | Nord | 433/18 |
| 5,002,485 | 3/1991 | Aagesen | 433/7 |

OTHER PUBLICATIONS

Guerreo, et al, "V. Transverse (Horizontal) Mandibular Deficiency," Modern Practice in Orthognatic and Reconstructive Surgery, 1992, pp. 2383–2394.
Guerrero, et al., "Distraccin Osteogenica Mandibular Intraoral," Odontologia, vol. 11, No. 2, May 8, 1995, pp. 16–132.
Guerrero, et al., "Distraccion Osteogenica Maxilar," Odontologia, vol. 11, No. 3, Sep. 12, 1995, pp. 211–218.
Grainger Equipment & Supply Catalog, No. 379, (Undated), p. 338.
Unknown Equipment & Supply Catalog, (Undated), p. 261.

*Primary Examiner*—Michael Buiz
*Assistant Examiner*—David O. Reip
*Attorney, Agent, or Firm*—Sidley & Austin

[57] ABSTRACT

A bone distraction device fixed by screws to a sectioned bone to facilitate multidirectional repositioning of the jaw bone. The expansion device is expandable to cause incremental expansion in the bone for lengthening or widening thereof. Support wires extending from the device can be clipped to desired lengths to accommodate the particular orientation of the device with respect to the bone. Forked or split anchor ends are then attachable to the wire arms and crimped or otherwise secured thereto. The anchor ends engage with respective bone screws so that when the expansion device is activated, the bone is forced apart.

31 Claims, 7 Drawing Sheets

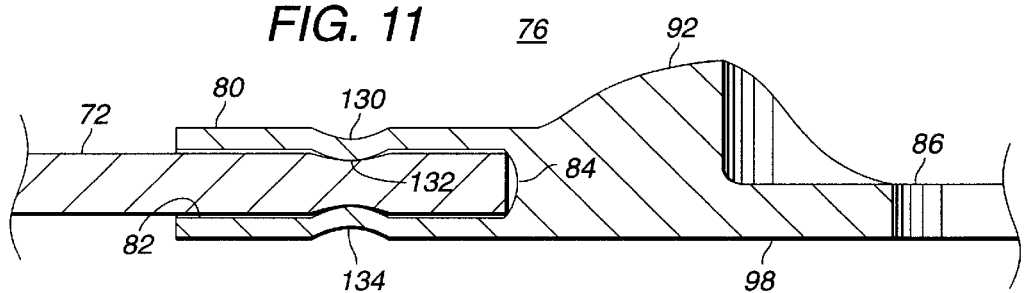
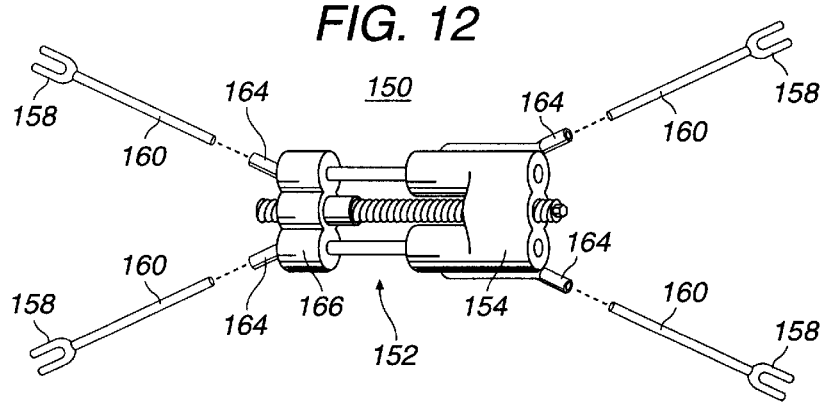
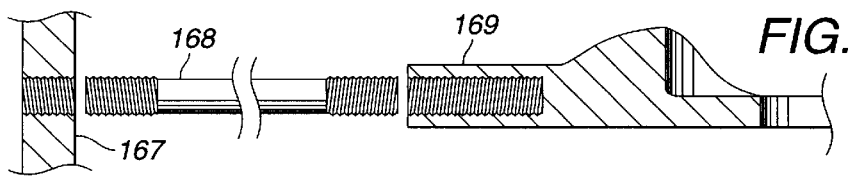
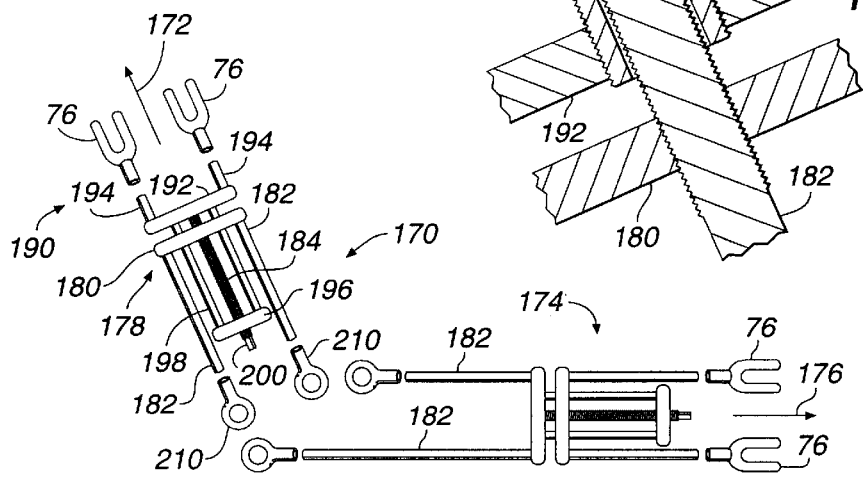

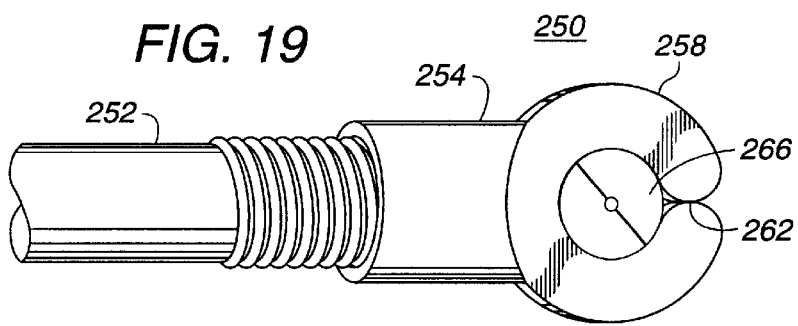
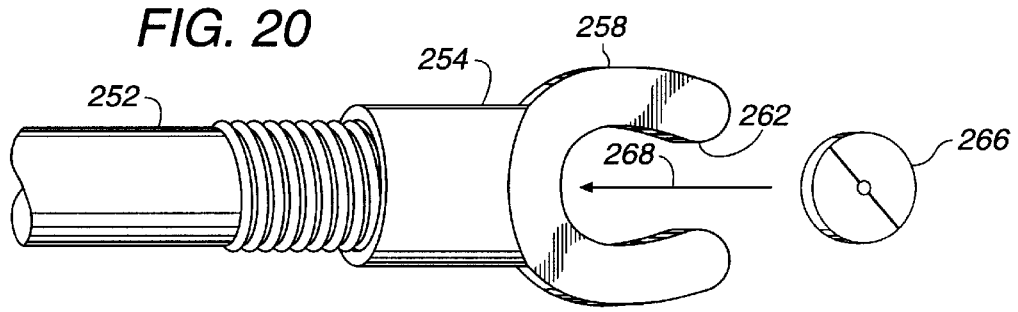
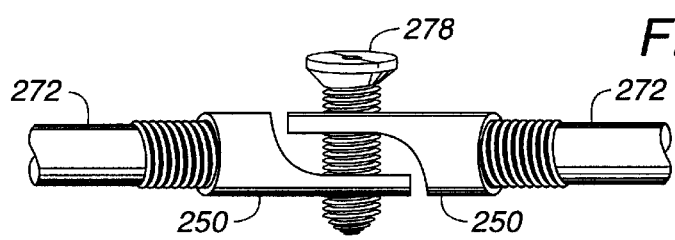
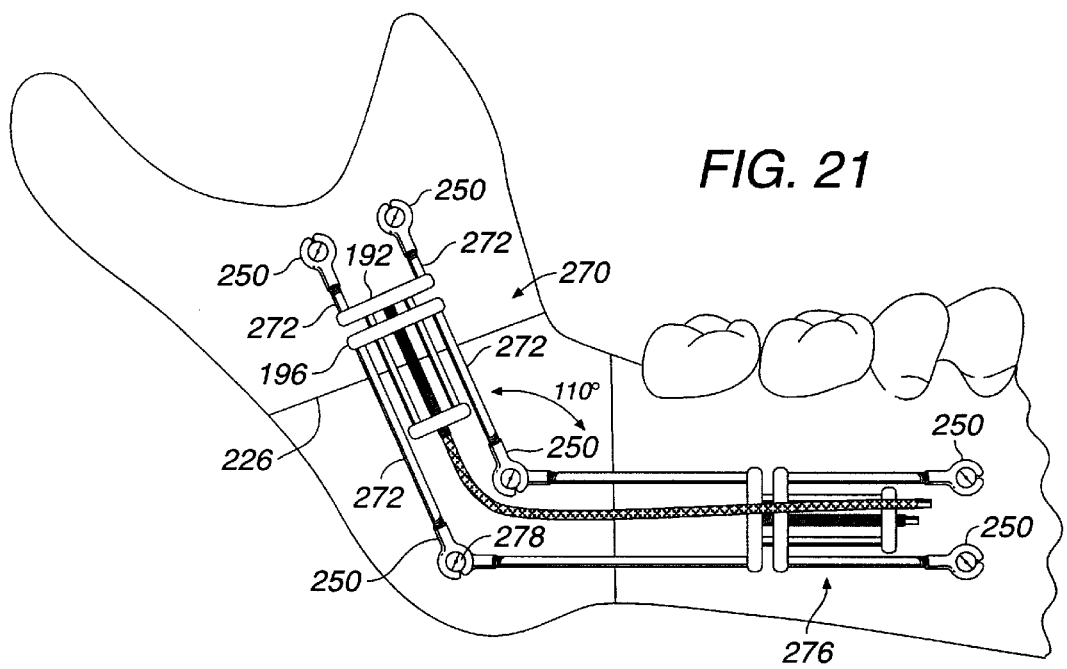

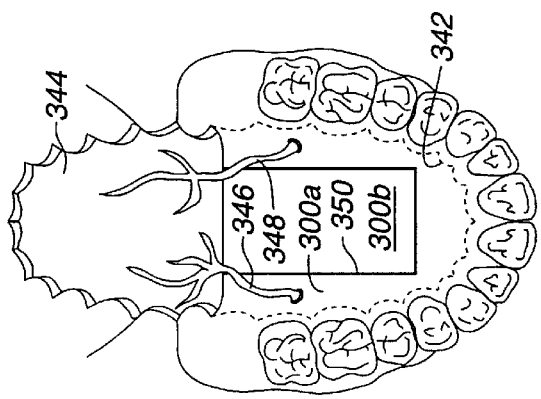
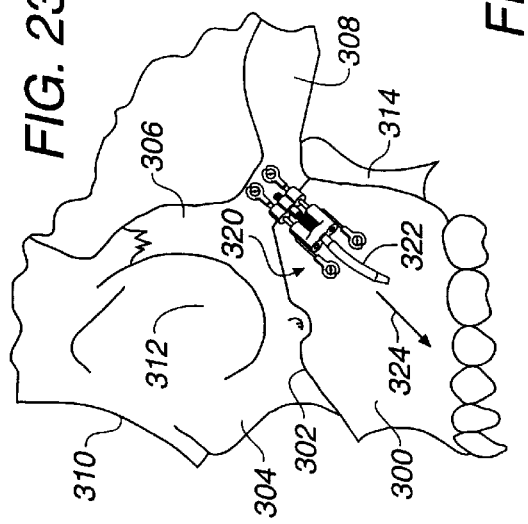
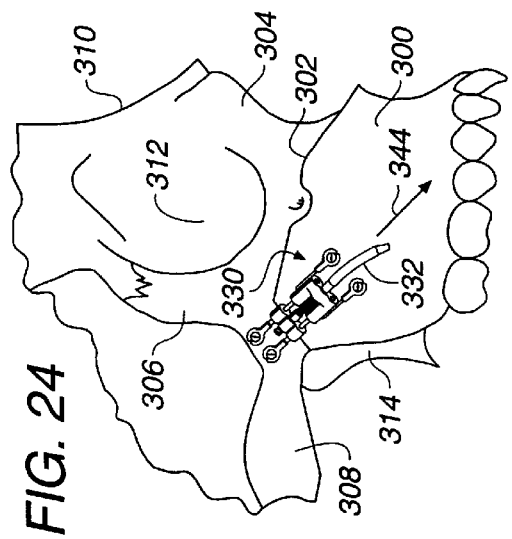
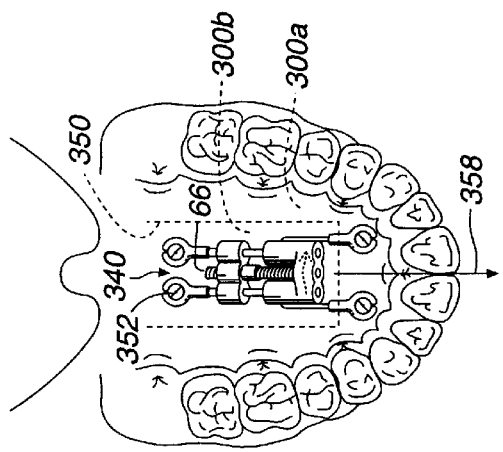

INTRA-ORAL BONE DISTRACTION DEVICE

TECHNICAL FIELD OF THE INVENTION

The present invention relates in general to appliances for correcting dentofacial deformities, and more particularly to bone borne expansion devices for achieving mandibular expansion and lengthening, as well as maxillary lengthening.

RELATED APPLICATION

This application claims the benefit of prior filed copending U.S. provisional application Ser. No. 60/033,287 filed Dec. 9, 1996.

BACKGROUND OF THE INVENTION

In recent years, there has been a significant development in the correction of dentofacial deformities. In particular, many devices and techniques have been developed for correcting deformities of the mandible. The Haas appliance is an example of one well-known device that provides lateral maxillary expansions. The Haas device is a mechanism constructed of two parts that is expandable by way of a threaded screw arrangement. The four arms attached to the device are anchored to the tooth structures to provide an expansion pressure between the teeth. The posterior portion of the mandible is completely severed, preferably between the alveolar tooth sockets of the bone. The Haas device, located between the left molars and right molars of the mandible can then be expanded to separate the mandible and provide lateral expansion. Because the Haas device is mounted to the tooth structures, it is known as a "tooth borne" device. The disadvantage with a tooth borne expansion device is that the teeth are not rigidly anchored to the mandible, and thus a proportionate symmetric expansion force cannot be achieved between the severed portions of the mandible. Mid-line, lateral and rapid mandibular expansion techniques utilizing the Haas appliance are disclosed in the text entitled *Modern Practice in Orthognathic and Reconstructive Surgery*, 1992, by Dr. William H. Bell, pp. 2383–2394.

In addition to the lateral expansion techniques, dentofacial deformities also exist in which the frontal portion of the mandible is retruded with respect to the corresponding maxilla. This is commonly called mandibular retrognasthism. There currently exist difference techniques for correcting this mandibular deformity by extension thereof in a forward direction. The procedure is well known as mandibular advancement, and includes sectioning the mandible on opposite sides, preferably between the ramus and the posterior molars. The cut is generally vertical, but laterally angled through the mandible. Then, the mandible is repositioned anteriorly the desired amount, and the segments of the bone are reattached by pins, screws or similar fasteners. Generally, the amount by which the mandible can be moved forward with this technique is limited to about 10–15 mm. The disadvantage with this procedure is that the amount of forward movement of the mandible with respect to the ramus must be accomplished at one time during the operation. The amount of forward movement is limited due to the inability of the muscle and surrounding tissues to stretch without relapsing. Sometimes, the amount of forward movement of the mandible for proper correction is significantly more than can be accomplished with this technique. Relapsing may also compromise the result. Additionally, mandibular advancement may not be feasible in children who frequently have significant psychological problems.

In order to overcome the problems of relapse and the foregoing problems, and allow treatment at an early age in an ambulatory setting, osteodistraction appliances have been developed that can mechanically reposition the mandible forward (when severed from the ramus) incrementally over a period of time. One such type of device is shown in FIG. 1. The lengthening appliance 10 is essentially a two-piece device that is extendible by way of threaded parts. A first part 12 is separable from a second part 14 by way of a threaded screw 16 that is engaged within a respective threaded bore (not shown) formed through each such part. An apertured collar 18 is fixed to the screw 16 and is rotatable by way of the radial holes 20 to provide adjustability between the parts 12 and 14. In addition, the first part 12 has fixed thereto a pair of rod-shaped guide rails, one shown as reference numeral 22, that are slidable through corresponding bores 23 formed longitudinally through the other part 14. In this manner, the one part 12 does not rotate with respect to the other part 14 when the screw 16 is rotated, or during regular movements of the mandible during chewing motions. Attached to the one part 12 is a pair of eyelets, one shown as reference character 24. Similar eyelets 26 are fastened to the other part 14.

In using the extension appliance 10, the mandible is severed by a saw or other suitable instrument. The one part 12 of the lengthening device is fastened to one portion of the severed mandible by the use of surgical screws that pass through the eyelets 24 and are secured to the bone. In like manner, the eyelets 26 of the other part 14 are fastened to the other portion of the mandible by another set of surgical screws. A similar extension appliance 10 is fastened in a similar manner to the opposite side of the severed mandible. Then the collar 18 is rotated a sufficient number of revolutions to reposition the mandible a predefined amount. Preferably, the appliances 10 are both adjusted the same amount. The rotation of the screw 16 is effective to separate the one part 12 of the appliance from the other part 14, thereby separating the severed portion of the mandible. At daily intervals, the collar 18 can again be rotated a prescribed amount to thereby incrementally lengthen the mandible. Over a period of time, such as three weeks, the mandible can be lengthened by as much as 25–30 mm.

While the extension appliance 10 shown in FIG. 1 is effective to incrementally lengthen the mandible, the inherent shortcoming is that the appliance must be held in place against the severed mandible as the screws are driven through the eyelets into the bone. Another disadvantage is that because the eyelets are rigidly fixed to the body of the appliance, there may be difficulty in placing the screws in the bone and avoid the developing teeth. To remove or replace the appliance, the surgical screws must be removed. This is an advantage of the appliance, procedure and can be carried out under local anesthetic in an ambulatory setting.

FIG. 2 shows an improved bone distraction device, as compared to that shown in FIG. 1. The bone distraction device 30 has a similar extension mechanism, but includes elongated wire arms, one shown as reference numeral 32. The one part 12 includes a pair of arms 32, each fixed thereto, and extending at an angle. Moreover, the end of each arm has an integral forked end 34. Forked end 34 includes a slot 36 for engaging with a surgical screw fastened or otherwise anchored to the mandible. The other part 14 includes a similar angled arm 32 with a forked end 34. However, the other part 14 includes a circular band 38 fastened to the part 14 by way of a wire arm 40, or the like.

FIG. 3 illustrates the bone distraction device 30 fastened to the base portion of the mandibular ramus 42 by a pair of surgical screws 44. On the other side of the cut bone 46, the device 30 is anchored by way of a screw 48, as well as the band 38 that is anchored to a tooth. The appliance 12 is anchored on the other side of the bone cut 46 by way of the two forked ends 34 anchored to the respective surgical screws 44. Such a device is known as a "tooth borne" bone distraction device.

The device 30 shown in FIGS. 2 and 3 has several inherent shortcomings. First, the band 38, being anchored to the tooth, is often problematic. Another shortcoming and often a serious problem, is that the forked ends 34 require that the screws 44 and 48 be precisely positioned and fastened to the severed parts of the mandible so as to accommodate the bone distraction device 30 therebetween. As can be appreciated, if one of the surgical screws is inadvertently fastened to the bone too far from the device, there may be a nonsymmetrical force applied across the cut in the bone. The tendency is thus to separate the bone parts in an unequal manner. Another disadvantage of the tooth borne appliance is that the involved tooth is not rigidly fixed to the mandible, but is somewhat movable. As such, the extension force on the tooth may not result in a symmetrical and proportionate separation of the bone, as some of the extension force is absorbed by tooth movement rather than bone movement.

As can be appreciated from the foregoing, a need exists for an improved bone distraction device and method of installation thereof, that overcomes the shortcomings and disadvantages of the prior art devices. A specific need exists for a bone distraction device that does not require specific spacing of the anchor screws in the mandible. Another need exists for a fully bone borne distraction device that is anchored solely to the bone to provide uniform, proportionate and symmetric separation of the severed bone parts. Another need exists for a device that is less critical of the precise location at which the surgical screws are driven into the bone. Yet another need exists for an expansion device constructed such that the anchor ends are adjustable with respect to the body of the device. A further need exists for a technique in which the bone can be sectioned at several locations, and multiple expansion devices employed to reposition the bone in multiple dimensions.

The principal indication for widening the mandible is absolute transverse mandibular deficiency. An excessively narrow and tapered arch form, dental crowding, tipped teeth and congenitally missing teeth are additional reasons for use of surgery which is intended to normalize basal bone position and facilitate non-extraction orthodontic treatment. Incomplete telescopic bite in certain congenital problems (Pierre Robin, Treacher Collins, Hemifacial Microsomia), and combined maxillo-mandibular transverse deficiency may be additional indications. Also, patients with mandibular transverse deficiency whose crowded teeth have been treated by extraction orthodontic therapy, may be additional indications. Many of these individuals may benefit from surgically assisted rapid mandibular expansion and orthodontic treatment.

Transverse mandibular deficiency is commonly managed by orthodontic mechanics which might include extraction and dental compensations. The result of this approach may be unstable owing to tipping of the teeth and bending of the alveolar bone. Proffit and Ackerman have reported a high risk of dental relapse when compensating orthodontic therapy has been performed to increase the inter-canine width in the presence of a primary transverse bone deficiency. Indeed, Proffit and White have documented the limitations and easy violation of the transverse envelope.

When a skeletal or dento-alveolar deformity is so severe that the magnitude of the problem lies outside the envelope of possible correction by orthodontics alone, surgical orthodontic treatment is indicated. Osteodistraction techniques may be the key to optimal nonextraction management of many malocclusions thus maintaining and increasing the functional occlusal table. Attention to transverse deficiency is vital in planning treatment for patients who require an increase in the lateral dimensions of the mandible or maxilla. The transverse envelope of discrepancy for mandibular alterations can be addressed by symphyseal osteotomy and gradual osteodistraction with the bone supported distraction device of the present invention.

When distraction appliances are not fixed to the bone (tooth supported appliance) there is typically disproportionate movement of the bone associated with expansion of the device. With the devices known in the prior art, tooth movement and tipping, additional to bone extraction, was frequently seen in patients. The osteodistraction appliances of the present invention produce proportionate movement of the teeth and bones. Additionally, the tooth borne appliance of the invention permits individualization of the osteotomy design and osteodistraction. With the new appliance design, not only can the mandible be lengthened and widened, but the maxilla can also be lengthened and widened. Indeed, a three-dimensional repositioning of the maxilla and mandible can be achieved in a more predictable manner and there is a proportionate movement of the mandible and maxilla transversely, vertically and anterior-posterior.

SUMMARY OF THE INVENTION

The shortcomings and disadvantages of the prior art bone distraction devices are overcome by the various features and aspects of the present invention. In accordance with the preferred embodiment of the invention, an expansion device is employed in conjunction with bone distraction techniques. The device includes a number of attachable forked anchor ends, each of which is engageable with a bone screw for positioning the device intra-orally. As the expansion device is adjusted to effect an expansion thereof, the forked anchor ends force the severed jaw apart, thereby achieving a uniform expansion of the bone.

In accordance with an important feature of the invention, the forked anchor ends are removably attached to the expansion device by way of female receptacle and male engaging members. The male member includes a wire arm or rod that can be clipped to the desired length and thereafter inserted into the receptacle. Then a sleeve portion of the receptacle can be crimped with a tool to thereby fix the male and female parts together. With this technique, the different arms or male members of the expansion device can be clipped to different lengths to thereby allow the device to be attached at numerous locations with respect to the severed bone. This feature of the invention overcomes the prior art shortcoming of requiring the bone screws to be located at relatively precise locations in the bone, as dictated by the configuration and shape of the expansion device itself.

In accordance with the preferred embodiment of the invention, the forked anchor ends each include a tubular receptacle that has a closed internal bore. The wire male members are permanently attached to the expansion device, but can be clipped at the distal ends thereof to the desired length. The internal bore with a closed end allows the wire end to bottom out in the bore and prevent any slipping therebetween due to the expansion force exerted between the bone screws by the device.

In order to accommodate different bone shapes and configurations, the receptacle portion of the forked anchor end can be angled with regard to the spaced-apart arms of the forked anchor end.

In accordance with another feature of the invention, two similar expansion devices, each equipped with attachable forked ends, can be attached via anchor screws to a bone having two different separation cuts therein. For example, a generally horizontal cut can be made in the ramus portion of the mandible, and a general vertical cut can be made in the horizontal portion of the mandible. The expansion devices can be anchored to a common set of anchor screws in the severed portion of the bone. With this arrangement, one expansion device can be employed to extend the vertical portion of the mandible, while the other expansion device can be employed to horizontally expand the other portion of the mandible. Again, the forked ends of the expansion devices facilitate the installation of the devices by using a precise location of the anchor screws in the mandible.

The present invention may also be equipped with different types of wire arms and/or attachable ends. According to another feature of the invention, the wire arms can be threaded into the body of the expansion device so as to be adjustable in length and provide an equal expansion force on each of the surgical screws to thereby result in a uniform and symmetrical separation of the bone parts. In like manner, the receptacle of the forked end can be threaded for fastening to a threaded end of the wire arm. With this construction, the effective distance between the forked end and the body of the expansion device can be adjusted. In addition, the ends of the wire arm can be threaded, one with right hand threads and the other with left hand threads, so that rotation of the wire arm itself accentuates the effective length thereof. The feature of the threaded wire arm allows easy replacement thereof in the event of breakage, damage or if the outer end is clipped too many times, or is clipped too short.

In accordance with another feature, the attachable anchor end is formed as a split ring to initially engage around a surgical screw. However, when a retraction force is exerted on the wire arm, the split ring is forced apart to a widened shape to thereby allow disengagement from the bone screw. In this manner, the bone screw does not require removal in order to remove the device from the patient. The removal of the device is accomplished in an ambulatory setting with local anesthetic. This is an additional advantage of the appliance in that it allows the procedure to be accomplished in a single stage.

The expansion device of the invention is readily adapted for use in surgical procedures where a patient's maxilla is to be repositioned. According to this technique, a first and second device constructed according to the invention are anchored across a sectioned portion of the maxilla, one on the posterior right side, and the other device on the posterior left side. A third device is anchored anteriorly across the sectioned maxilla in the palatal area of the patient's oral cavity. Each of the three expansion devices can then be activated to incrementally lengthen or otherwise reposition the maxilla of the patient.

In accordance with an important feature of the invention, a distraction appliance is designed to achieve multidirectional movement of the mandible. The appliance is relatively small to facilitate intra-oral installation and is readily activated, and can be readily utilized for correcting multiple dimensioned mandibular deformities.

From the foregoing, the expansion device according to the invention substantially reduces the problems and shortcomings of the prior art devices and facilitates a more economical and expeditious installation of the expansion device in a single stage.

BRIEF DESCRIPTION OF THE DRAWINGS

Further features and advantages will become apparent from the following and more particular description of the preferred and other embodiments of the invention, as illustrated in the accompanying drawings in which like reference characters generally refer to the same parts, functions or elements throughout the views, and in which:

FIG. 11 is a cross-sectional view of the forked anchor end crimped to a wire arm inserted therein;

FIG. 12 is another embodiment of the lengthening device according to the invention, wherein female receptacles are attached to the expansion device, and wire arms integral with forked ends are insertable and crimped within the receptacles;

FIG. 13 is a partial cross-sectional view of a wire leg that is threadably fastened to both the body of the expansion device, as well as to the attachable forked anchor end;

FIG. 14 illustrates another embodiment of the invention, wherein two expansion devices constructed according to the invention are employed to achieve a two-dimensional expansion of angled bones;

FIG. 15 is an enlarged view of an alternate construction of a portion of the bone distraction device shown in FIG. 14;

FIG. 19 illustrates the engagement of the split ring anchor end of FIG. 17 engaged around a bone screw;

FIG. 20 illustrates the deformation of the split ring fingers when the anchor end is forcefully removed from the surgical screw;

FIG. 21 is a plan view of a pair of bone distraction devices equipped with the split ring anchor ends installed to a mandible to provide a two-dimensional extension thereof;

FIG. 22 is a side view of the split ring anchor ends of two expansion devices of FIG. 21, both engaged with a common surgical screw;

FIGS. 23 and 24 illustrate respective left and right views of a sectioned maxilla with distraction devices mounted thereto for lengthening the maxilla downwardly and forwardly;

FIG. 25 is a view of the palatal portion of the maxilla, with a mucosal tissue flap lifted back to section the maxilla; and FIG. 26 is a view of the palatal portion of the maxilla with the mucosal tissue flap replaced and the bone distraction device installed so as to span the sectioned maxilla.

DETAILED DESCRIPTION OF THE INVENTION

Figure 1:
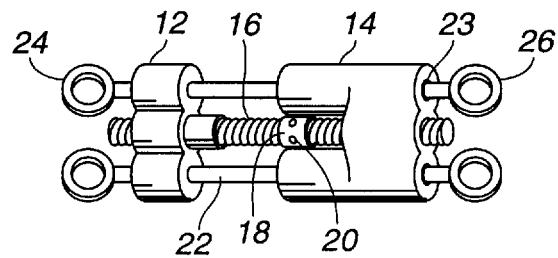
FIG. 1 is an isometric view of a well-known expansion device, wherein plural eyelets are fixed directly to the device and require the bone anchor screws to be installed with the expansion device in place.
Figure 2:
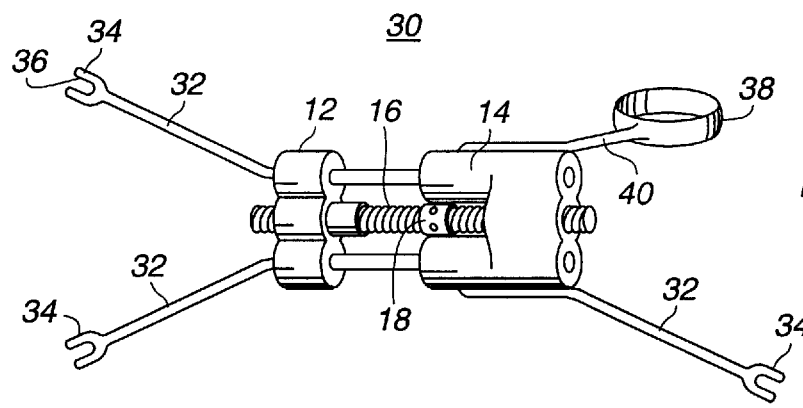
FIG. 2 is an isometric view of a well-known expansion device, including three arms with integral forked arms and a fourth arm having a band for anchoring to a tooth.
Figure 3:
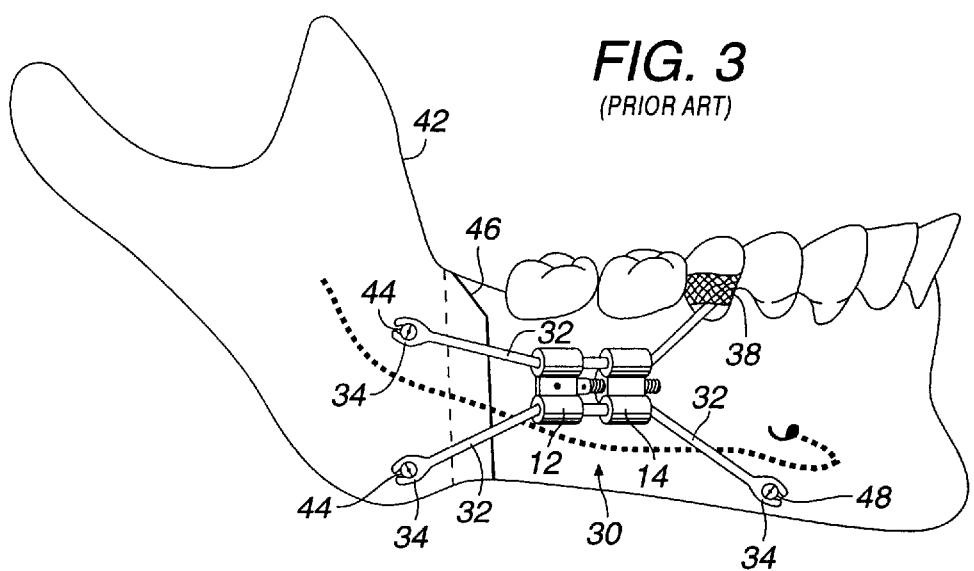
FIG. 3 illustrates the expansion device of FIG. 2, as fixed to both the mandible and a tooth.
Figure 4:
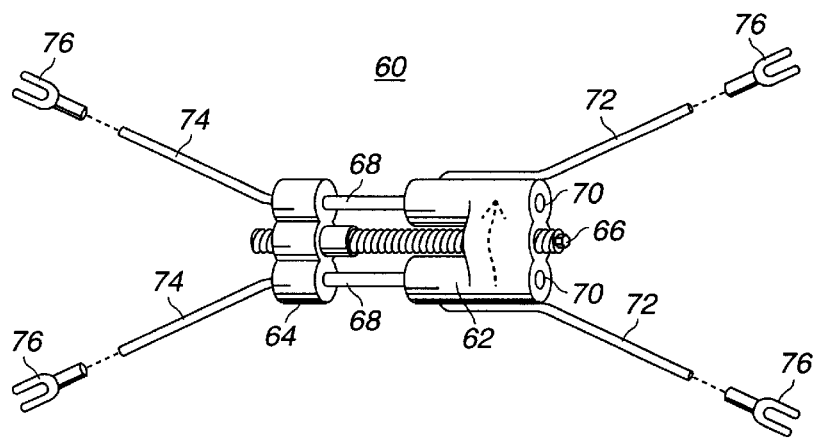
FIG. 4 is an isometric view of the expansion device constructed according to the preferred embodiment of the invention, including forked anchor ends attachable to wires that can be clipped to the desired length.

FIG. 4 illustrates an embodiment of the invention that is highly advantageous over the prior art devices. The expansion device 60 includes a conventional first part 62 that is movable with respect to a second part 64 by way of a threaded screw 66. The threads of the screw 66 are such that one turn thereof causes a 0.5 mm expansion of the device 60. In this manner, the bone can be lengthened in predetermined amounts by rotating the screw 66 a predescribed number of times. Generally, the parts of the expansion device 60 are constructed of surgical stainless steel, titanium or other material suitable and compatible for use with body tissues. A pair of guide rails 68 are formed integral with the second part 64, and are slidably insertable within respective parallel bores 70 formed longitudinally through the first part 62. With this arrangement, either torsional or angular displacements of the first part 62 with respect to the second part 64 are minimized. The first part 62 and second part 64 both include threaded bores formed centrally therethrough for engagement with the screw 66 to effect longitudinal expansion between the first part 62 and the second part 64. As noted in FIG. 4, the screw 66 has a hexagonal male end for adjustment. The screw end can also be formed with a hex or other internal shape for engagement with a complementary-shaped adjustment tool (not shown).

In a preferred form of the invention, the expansion device 60 includes a pair of wire arms 72 attached to the first part 62 by either welding or other suitable attachment. The arms 72 are shown welded to the opposing sides of the first part 62. The arms 72, preferably formed of stainless steel or other metal and non-reactive to tissues, are angled somewhat outwardly, as shown. In addition, the arms 72 are formed of a material that is rigid and generally resistant to bending or deformation along the length thereof. In a preferred form of the invention, the arms 72 are preferably about 30 mm long and about 2 mm in diameter.

Another pair of arms 74 are formed integral with the second part 64. The arms 74 are formed of the same type of metal as arms 72, but are fixed within holes or bores (not shown) formed in the end of the second part 64. The ends of the arms 74 can be fixed to the second part 64 by being slightly oversized with respect to the bores, or being swaged, welded, bonded or threaded therein.

In accordance with an important feature of the invention, each pair of arms 72 and 74 is adapted for removable attachment to corresponding forked anchor ends, each shown as reference numeral 76.

Figure 5:
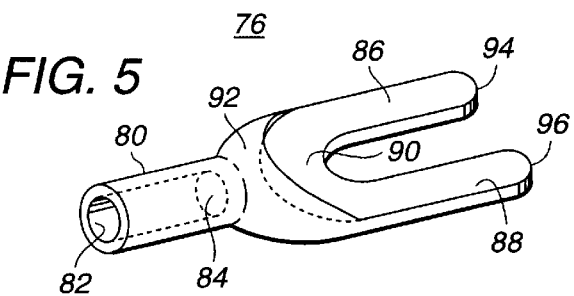
FIG. 5 is an isometric view of a forked anchor end constructed according to the preferred embodiment of the invention.
Figure 6:
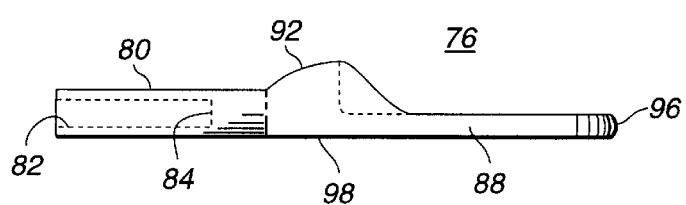
FIG. 6 is a side plan view of the forked anchor end shown in FIG. 5.
Figure 7:
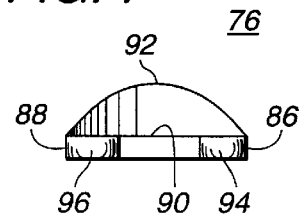
FIG. 7 is a frontal end view of the forked anchor end shown in FIG. 5.

The attachable forked anchor end, constructed according to the preferred embodiment of the invention, is shown in detail in FIGS. 5–7. The forked end 76 is constructed of a titanium material, or other suitable material adapted for use in surgical operations. The forked anchor end 76 includes a tubular receptacle 80 with a bore 82 formed therein. The bore 82 is slightly oversized with respect to the diameter of the wire arm 72. Importantly, the bore 82 terminates internal to the receptacle 80 and thus has an internal closed end 84. This construction is important in allowing the end of the wire arms 72 to bottom out within the bore 82 as the expansion device 60 exerts an outward distraction force on the surgical screws fastened into the bone. Formed integral with the tubular receptacle 80 are a pair of spaced-apart arms, shown in FIG. 5 as reference characters 86 and 88. The lateral spacing between the arms 86 and 88 are sufficient to engage around the shank of a conventional bone screw, but is smaller than the diameter of the screw head. The top and bottom surfaces of the arms are substantially planar, as shown in FIG. 7. The arms 86 and 88 are connected by a planar portion to accommodate the flat undersurface of the bone screw head. The connecting portion of the forked anchor end 76 between the tubular receptacle 80 and the spaced-apart arms 86 and 88 provide sufficient strength and rigidity to the member to prevent bending thereof due to a longitudinal force exerted between the bone screw and the expandable device 60. The ends 94 and 96 of the spaced-apart arms are generally blunt to prevent gouging, tearing or damage to the tissue. As noted in FIG. 6, the forked end 76 includes a generally planar bottom 98 to eliminate any rough edges that would interfere with the skin and soft tissue covering the bone.

Figure 8:
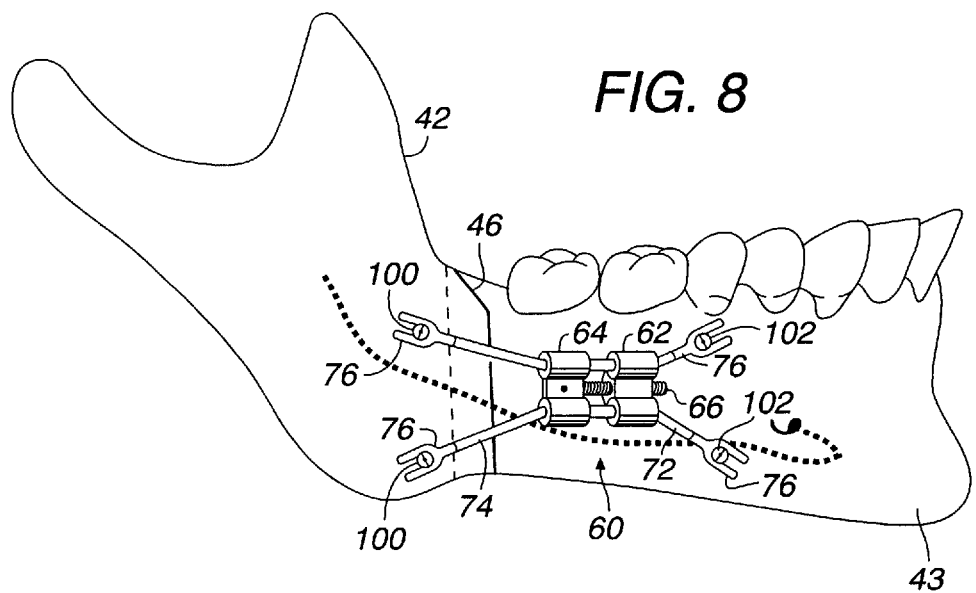
FIG. 8 is a plan view of the expansion device according to the preferred embodiment attached to the mandible for lengthening thereof.

FIG. 8 illustrates the expansion device 60 installed intra-orally to cause a horizontal separation (distraction) of the mandible 42 about the vertical cut 46 therein. As can be seen, the two wire arms 74 extending from the second part 64 of the expansion device 60 are attached to the bone 42 on one side of the cut 46. The two wire arms 72 attached to the first part 62 of the expansion device 60 are connected to that part of the bone 43 on the other side of the cut 46. Moreover, each pair of wire arms 74 is anchored to the same portion of the bone 42 by a respective screw 100. In like manner, the other pair of arms 72 are attached to the other portion of the bone 43 by respective screws 102. While not shown, the portions 42 and 43 of the bone are covered by the mucosal and gingival tissue (not shown). Nevertheless, the screws 100 and 102 are driven through the gingival and mucosal tissue into the bone, and the expansion device 60 is anchored to the outermost portion of the screws that protrude somewhat outside the tissue. The procedure for preparing the mandible for expansion with the device according to the invention is set forth more fully below. It is noted that the adjustment screw 66 faces anteriorly so that the expansion device 60 can be expanded by way of a flexible adjusting tool when the patient's mouth is open. As can be appreciated, when the expansion device is expanded, a substantial resisting force is experienced, due to the stretching of the gingival tissue surrounding the mandible, as well as muscle tissues.

The expansion device 60 can be removed after the separated bone has grown together across the distraction gap. The device 60 can be removed by turning the screw 66 in a direction to cause retraction of the first and second parts 62 and 64. When retracted, the forked anchor ends 76 are clear of the bone screws and the device 60 can be easily removed. The anchor screws need not be removed. It can be appreciated that the device 60 can be reused with the forked ends crimped thereto, or one or more forked ends can be clipped off so that the arm is made shorter to accommodate particular bone configurations or placements of the device with respect to peculiar bone cuts. A new forked end 76 can then be crimped to the end of the clipped arm, whereupon the newly configured device can be reused. As will be described more thoroughly below, the expansion device 60 can be constructed so that the wire arms are threadably fastened to the body of the device 60. In this manner, if a wire arm becomes too short due to numerous clippings, it can simply be replaced with a new arm. This allows the expansion device to be reused many times.

The expansion device 60 is preferably utilized according to the following method of installation and removal. A horizontal mucopericostal incision of about 3 cm is made in the area where it is intended to section the mandible. The incision is made on the outside of the mandible, adjacent the cheek tissue. A subperiosteal tunnel is then formed upwardly, as well as downwardly, via the incision. The tunnel allows sufficient spatial room in the area of the intended osteotomy. If desired, titanium bone markers can be driven into the mandible, on each side of the intended osteotomy site. The markers can provide a mechanism to measure the extent of the lengthening of the mandible during activation of the bone distraction device.

Next, the osteotomy procedure is carried out, whereby the mandible is sectioned. It is noted that the mandible is not completely sectioned therethrough, as it is important that the nerve that extends within the mandible cortex remains intact. The inferior border of the mandible is first sectioned with a reciprocating surgical saw. Next, the lateral cortex portion of the mandible is sectioned followed by the alveolar crest portion of the mandible. This leaves only the lingual portion (facing the oral cavity) of the mandible intact, which is then broken using an osteotome. The sectioned mandible thus results in proximal (posterior) and distal (anterior) portions of the bone. With this protocol, no incision is required on the lingual side of the mandible. The mandible is thus sectioned, leaving intact the nerve and surrounding cortex.

The expansion device 60 is then placed across the sectioned mandible, and a pair of titanium bicortal positional screws are set into the proximal portion of the mandible, via the incision. Preferably, the bicortal positional screws are about 2 mm in diameter and about 13–15 mm in length. The arms 74 and crimped forked ends (FIG. 4) of the expansion device 60 are inserted under the mucosal tissue and anchored to the positional screws set into the proximal segment of the mandible. The expansion device 60 is stabilized by setting two other positional screws in a transmucosal manner, i.e., driving the screws through the mucosal tissue into the underlying distal section of the mandible. The head of the distal positional screws extends a small distance from the surface of the mucosal tissue. The expansion device 60 is thus stabilized by the proximal and distal positional screws, in a position spanning the osteotomy in the mandible. As can be appreciated, the forward arms 72 and attached forked ends 76, as well as a portion of the first part 62 of the expansion device 60 are not covered by the mucosal tissue, but rather are exposed and accessible in the space between the cheek and the mucosal tissue of the mandible.

The expansion device is activated by rotating the adjusting screw 66 about two turns in an attempt to separate the proximal and distal sections of the mandible about 2 mm. By visually inspecting the bone markers, or by x-ray analysis, if it is determined that the ramus has indeed separated by this amount, it is concluded that all portions of the mandible have been successfully sectioned. The wound margins are then sutured together to close the incision. The ramus of the patient's mandible on the other side can be sectioned in a similar manner to provide an intra-oral installation of a second expansion device.

The protocol for lengthening the mandible includes the activation of the device 60 by rotating the screw 66 a prescribed number of turns, or partial turns. As noted above, each full turn of the screw 66 is effective to lengthen the mandible about 0.5 mm. The extent of each activation depends on the total desired lengthening of the mandible, the condition of the mandible, the age of the patient, and other parameters. The latency period between each activation is expected to be about 5–7 days. As can be appreciated, the adjusting screws 66 face forwardly in the patient's oral cavity, and are readily accessible with a tool for rotating the screw to expand the device 60. The tool can have a socket-type end matable with the head of the screw 66, and a flexible handle. It is noted that it is not necessary to lengthen each side of a patient's mandible by the same amount, especially if there is an initial deformity that can be corrected by a nonsymmetrical lengthening of each side of the mandible.

After the desired lengthening of the mandible has been achieved, and the bone tissue has healed sufficiently so as to be stable, the expansion devices are removed. The removal of the expansion device 60 is achieved by first clipping the anterior arms 72, removing the anterior positional screws, or by simply removing the anterior screws and extracting the device 60 from the mucosal tissue. Since the forked ends 76 at the posterior portion of the device are open ended, they can be released from engagement with the posterior positional screws by simply pulling forward on the expansion device 60. It is not necessary to remove the posterior positional screws, as they are embedded within the mucosal tissue. The anterior positional screws, being installed in a transmucosal manner, are readily available and can be easily removed with a screw driver or similar tool. The opening in the mucosal tissue, through which a portion of the body of the expansion device protrudes, can then be closed by sutures.

Figure 9:
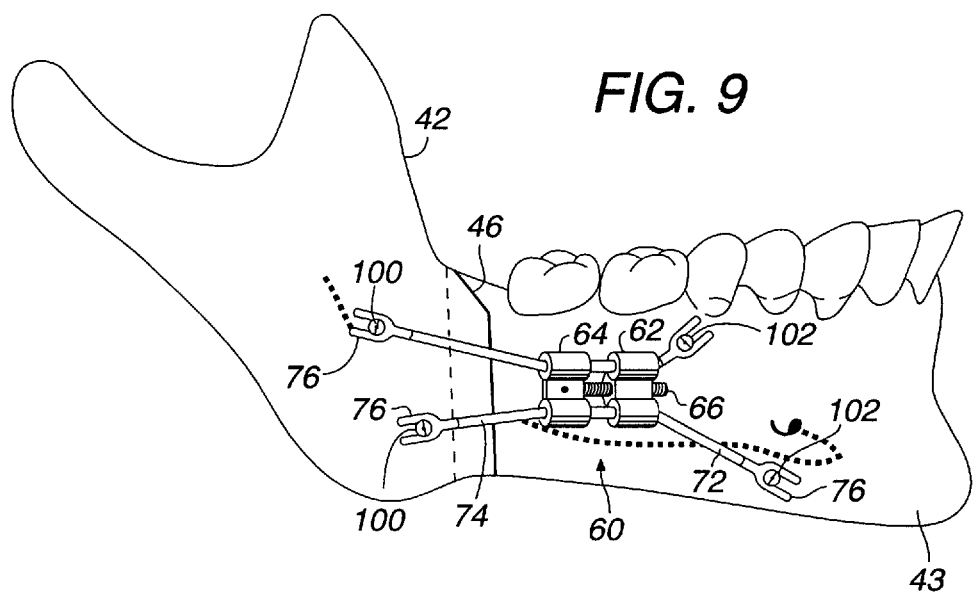
FIG. 9 is another view of the expansion device according to the invention, with the wire arms cut to different lengths to accommodate oblique cuts in the mandible.

Returning now to the description of the invention, when the mandible is sectioned vertically as shown in FIG. 8, the expansion device 60 is aligned generally horizontally along the portion of the mandible that holds the teeth therein. As such, the arms 72 and 74 of the device 60 can be cut to accommodate the placement of the screws 100 and 102 at convenient locations in the bone. Certain situations may dictate that the bone cannot be sectioned at a convenient vertical location, but must be sectioned at an angle, such as shown in FIG. 9. In order to separate the bone uniformly at the cut, the bone distraction device should be installed so that the axis of expansion is generally perpendicular to the cut through the bone. When the bone is sectioned at an angle such as shown in FIG. 9, the patient's teeth often interfere with the anchoring of at least one of the arms of the bone distraction device. To circumvent this problem, the one arm can be cut very short and an anchor end attached thereto so that the bone can yet be utilized as a point of force exerted thereon by the expansion device 60. Many other situations can now be accommodated by the versatility of the present invention as compared to the prior art devices. The present invention facilitates distraction in a single stage.

Figure 10:
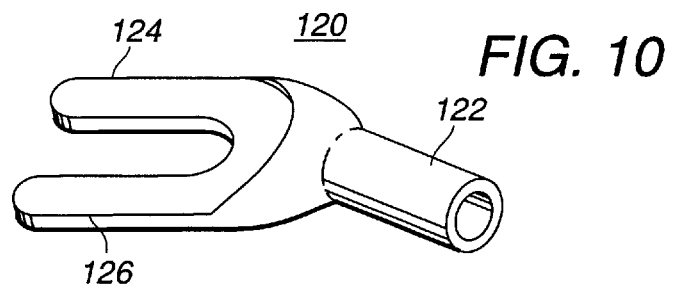
FIG. 10 illustrates another embodiment of the forked anchor arm, with the sleeve receptacle thereof being angled with respect to the spaced-apart arms.

FIG. 10 illustrates a forked anchor end 120 constructed according to another embodiment of the invention. The forked end 120 is similar to that shown above in connection with FIG. 5, except the tubular receptacle 122 is formed at an angle with respect to the spaced-apart arms 124 and 126. Rather than bending the wire arms 72 or 74 to achieve a desired angle, the forked end 120 is itself angled. The forces exerted on the angled forked end 120 can be better sustained, rather than requiring the wire arms 72 or 74 to be bent and to maintain the desired angle under the expansion forces. It is believed that the angled forked end 120 is better able to withstand extension forces than a bend in the wire arms 72 or 74. Those skilled in the art may prefer to have available forked ends with many different types of angles to accommodate the various contours of the tissue or bone.

FIG. 11 is a cross-sectional view of a forked anchor end 76 of the invention crimped to a wire arm 72. The end of the arm 72 is preferably roughened with a dental bur, and then grooves are drilled or otherwise formed in the end of the wire to facilitate stability of the arm on the forked end 76. The end of the arm 72 is then inserted into the receptacle 80 of the forked end 76. A crimp is then formed on the top side of the receptacle 80 by mashing the sidewall thereof inwardly to form a depression 130 therein. The force applied to the sidewall of the receptacle 80 is effective to slightly deform the arm 72 at the location denoted by reference character 132. A similar crimp 134 can be formed on the bottom side of the receptacle sidewall. In this manner, the forked end 76 is prevented from falling off of the wire arm 72. The crimp operation is carried out after the wire arm 72 has been cut to the desired length, and has been inserted fully into the bore 82 until it has bottomed out therein. Many different types of crimping tools can be employed to crimp the forked end 76 to the end of the wire arm 72. A pair of wire cutters with dulled edges can be employed to carry out the crimping operation as noted above. Importantly, the crimping operation can be performed prior to the actual installation of the expansion device 60 to the bone. Also, the crimping operation need not be carried out on both the top and bottom surfaces thereof, but can also be employed on the side surfaces. It may be found that only a single crimp is necessary to fasten the forked end 76 to the wire lead 72.

Those skilled in the art may prefer to fasten the forked end 76 to the wire arm 72 prior to use of the expansion device without crimping the arm parts, by using a cement, adherent or other bonding agent. The wire arm 72 can be bonded to the forked end 76 by coating the end of the wire with the bonding agent, inserting the wire into the bore 82 of the receptacle 80 until it bottoms out, and then allowing the cement to cure or dry. In order to attach the arm and forked end parts together, the parts may be constructed with an interference fit, or with ribbed/notch or knurled surfaces to provide a sufficient engagement therebetween to keep the ends from falling off during installation.

As yet another alternative, the expansion device can be constructed to achieve expansion by use of a shape-memory alloy, rather than an adjustment screw. Shape-memory alloys are well known for the characteristic that the material expands when subjected to heat, but does not contract when the source of heat is removed. The two body parts of the expansion device can be connected together using a shape-memory alloy. After the expansion device is installed across a bone osteotomy using anchor screws, the shape-memory alloy can be heated a certain extent to cause expansion. The shape-memory alloy can thereafter be heated again to cause another permanent expansion, thereby achieving repositioning of the bone. The source of external heat can be body temperature, laser or another suitable heat source. It is believed that a laser can achieve submucosa heating of the shape-memory alloy to cause lengthening of the expansion device. Those skilled in the art may also desire to construct the arms of the expansion device with the shape-memory alloy material to achieve lengthening.

FIG. 12 illustrates yet another embodiment of an expansion device 150 constructed in accordance with the principles and concepts of the invention. Here, the expandable base part 152 is substantially identical to that shown in FIG. 4, with the exception of the manner in which the wire arms and forked ends are attached thereto. In the embodiment of FIG. 12, the expansion device 150 has attached to the first part 154 a pair of tubular receptacles 156 angled in the manner shown. Each receptacle 156 is welded, threaded or otherwise fastened to the first part 154 of the expansion device 150. In this embodiment, the forked ends 158 are formed integral with respective wire arms 160. The wire arms are of a predetermined length, preferably somewhat longer than that required in typical bone distraction operations. The forked ends 156 extend a specified distance from the first part 154 of the expansion device 150 by clipping the wire ends 162 to the desired length, and then inserting the clipped end into the respective socket 156. The ends 162 of the wire arms 160 can be secured to the respective receptacles 156 by crimping, bonding, cementing or otherwise, as described above. Similar receptacles 164 are formed integral with the second part 166 of the expansion device 150. Forked ends 158 formed integral with wire arms 160 are cut to desired lengths and fixed within the respective receptacles 164 in a manner similar to that described in connection with the first part 154. In addition, those skilled in the art may prefer to dispense with the receptacles 164, and provide bores within the respective first and second parts 154 and 166. The wire arms 150 can then be cut to length and bonded or otherwise mechanically fixed within the respective receptacles. It is also possible to provide tubular receptacles at both ends of the wire arms, one receptacle connected to the device as shown, and the other made integral with the anchor end, as shown in FIG. 5.

The wire arm embodiment device of FIG. 13 can be constructed to provide fastening of the wire arms to the body of the expansion device by way of threaded parts. In FIG. 13, there is shown a partial cross-sectional view of such an arrangement. The body part 167 of the device is formed with left hand threads, as is a base portion of the wire arm 168. The distal end of the wire arm 168 is fastened to an attachable anchor end 169 by right hand threads. With this arrangement, the wire arm 168 is not only replaceable, but is also effectively lengthened or shortened by rotational turning of the wire arm 168. This individual adjustability of the effective length of each arm 168 allows the expansion device to be very accurately tailored to the position of the surgical screws driven into the bone.

FIG. 14 illustrates an arrangement of two expansion devices for achieving the extension of bone portions in different directions. Shown is a first expansion device 170 for achieving vertical bone lengthening in the direction of arrow 172. A second expansion device 174 is effective to achieve horizontal bone lengthening in the direction of arrow 176. The expansion devices 170 and 174 are constructed substantially identical. As such, the structure of the first expansion device 170 will be described.

The first expansion device 170 includes a first part 178 having a base portion 180 to which are attached a pair of wire arms 182. As will be described below, the wire arms 182 are clippable to the desired length for attachment thereto of anchor ends. The base portion 180 includes a threaded hole therein for receiving an adjustment screw 184. When the screw 184 is rotated, the base portion 180 advances up or down the shank of the screw 184. The other part 190 of the expansion device 170 is includes a base portion 192 with a pair of wire arms 194 extending therefrom. The wire arms 194 can be clipped to length as described above. Attached to the base portion 192 of the second part 190 includes a support 196 fixed thereto by way of a pair of standoffs 198. Both ends of the screw 184 are supported respectively in a non-threaded manner to the base portion 192 and the support 196. Stated another way, when the screw 184 is rotated, it freely rotates within the base portion 192 and the support 196 without advancing with respect thereto. While not shown, the base portion 180 of the first part 178 has a respective hole therein so that each standoff 198 can freely pass therethrough. With this construction, when the screw 184 is rotated, the first part 178 moves longitudinally with respect to the second part 190, depending upon which direction the screw 184 is rotated. The screw 184 is formed with a hexagonal head 200 for rotational adjustment thereof.

As noted above, each wire arm pair 182 and 194 is adapted for clipping to the appropriate length. Forked anchor ends 76 can be crimped or otherwise secured to the clipped ends of the wire arms 194, in the manner described above. Anchor ends 210 of the type having closed ends formed integral with tubular receptacles can be attached to the wire arms 182. As will be set forth more thoroughly below, these forked anchor ends 76 and the anchor ends 210 can be replaced with another type of attachable anchor end.

The second expansion device 174 is formed substantially identical to the first expansion device 170 but installed at an angle thereto, such as generally shown in FIG. 14. With this arrangement, one wire arm 182 of the pair is required to be shorter than the other arm 182 to thereby accommodate such an angle of attachment.

FIG. 15 illustrates, in enlarged form, an alternative construction of the expansion device 170 for allowing a threaded attachment of the arms 182 and 194 thereto. The arm 182 can be threaded at the end thereof for engagement with threads formed in the base support 180. The arm 182 is not only replaceable, but adjustable in length. The arm 194 is similarly threaded into the respective base support 192 for similar advantages. In addition, the arm 194 is larger in diameter than arm 182, and has a bore formed therein to receive the threaded end of the arm 182 when the device is completely retracted. In this manner, the arms 182 and 194 do not interfere with each other and thus allows a greater variation in adjusting the effective lengths of the arms 182 and 194. The other arms of the device are constructed to cooperate in a similar manner.

Figure 16:
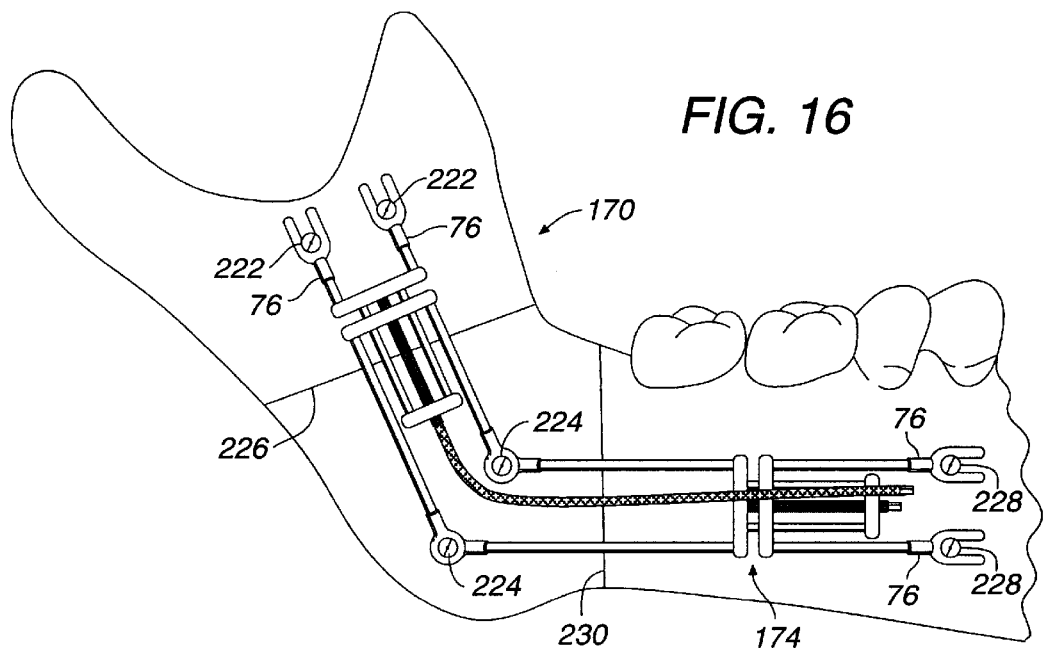
FIG. 16 illustrates the dual expansion device of FIG. 14 installed on a mandible having a generally horizontal cut and a generally vertical cut therein.

FIG. 16 illustrates the first expansion device 170 and the second expansion device 174 as anchored at three general locations to a mandible 220. The first expansion device 170 has forked anchor ends 76 anchored to an upper portion of the ramus by surgical screws 222. The opposite end of the expansion device 170 is anchored to the severed bone by surgical screws 224. A generally horizontal cut 226 in the ramus is incrementally separated by adjustment of the first expansion device 170.

The second expansion device 174 is anchored to the generally horizontal portion of the mandible by way of forked anchor ends 76 and surgical screws 228. The other end of the second expansion device 174 is anchored in common to the severed bone with the first expansion device 170, by the set of surgical screws 224. The second expansion device 174 spans the vertical cut 230 in the mandible and is effective to cause a lengthening of the mandible between such cut. With this technique, it can be seen that the ramus part of the mandible is generally lengthened in a vertical direction by the first expansion device 170, and the lower portion of the mandible is lengthened horizontally by the second expansion device 174. A bi-directional expansion technique is thereby achievable to provide multi-direction bone expansion capabilities.

As further noted in FIG. 16, a flexible adjustment tool 240 can be utilized to reach the first expansion device 170 and rotated to cause expansion or contraction thereof. The same tool 140 can be employed to provide corresponding or different adjustments to the second expansion device 174. It can be appreciated that the first expansion device 170 can be adjusted at a different rate or by different increments as compared to the second expansion device 174.

It is contemplated that not only can vertical and horizontal lengthening of the mandible be achieved, but lateral widening can also be achieved. In order to utilize the dual distraction devices 170 and 174 to effect widening of the mandible, the arms 182 of the device 170 (FIG. 14) are prebent outwardly. In like manner, the arms 182 of the other device 174 are also prebent outwardly. The devices 170 and 174 are then installed in the manner noted above by first anchoring the forked ends 76 of both devices 170 and 174. The other anchor ends 210 of both devices are then anchored to the sectioned portion of the ramus, as shown in FIG. 16. The prebent arms 182 of both devices 170 and 174 impose an outward force on the sectioned portion of the mandible, thereby moving such portion of the mandible outwardly. The degree by which the arms 182 are prebent outwardly governs the amount by which the sectioned mandible is laterally widened or repositioned. Preferably, pairs of bone distraction devices are utilized on each side of a patient's mandible to provide a balanced lateral movement of the mandible.

It can also be appreciated that the arms 182 of the devices 170 and 174 can also be prebent inwardly to thereby move the sectioned portion of the mandible inwardly to provide a narrowed lower jaw bone.

Figure 17:
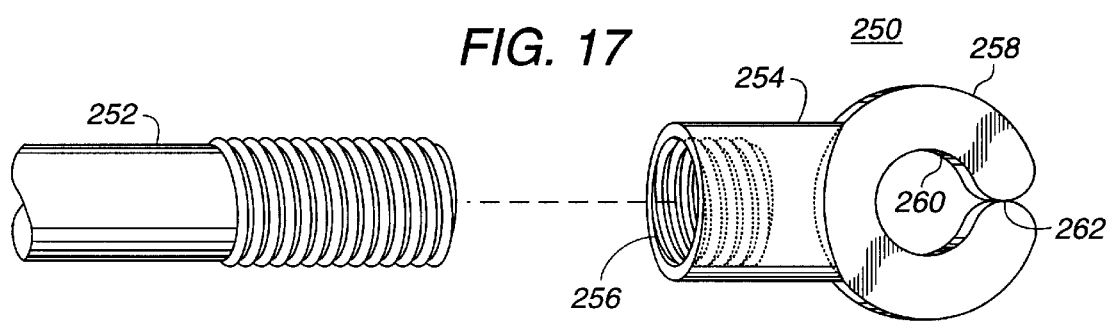
FIG. 17 illustrates another embodiment of the invention having a split ring anchor end that is threadably attached to a wire arm.
Figure 18:
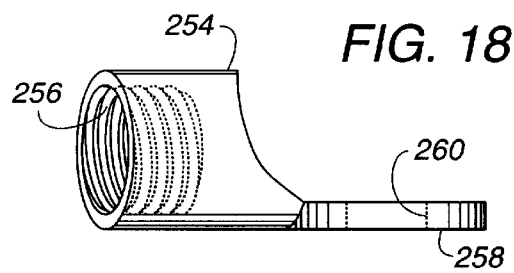
FIG. 18 is a side plan view of the split ring anchor end of FIG. 17.

With reference now to FIG. 17, there is illustrated another embodiment of an attachable anchor end, constructed according to the principles and concepts of the invention. In this embodiment, the anchor end 250 is threadably mated with the threaded end of a wire arm 252. Both the anchor end 250 and the threaded wire 252 are shown much enlarged to depict the features of the invention. The anchor end 250 includes a barrel 254 with internal threads 256. The barrel 254 is preferably open and threaded therethrough, as shown in FIG. 18. This open-ended construction allows a significant degree of axial adjustment with regard to the threaded wire 252. Welded or otherwise attached to the barrel 254 is an annular split ring 258 of generally planar construction. The split ring includes a central opening 260 for the passage therethrough of a bone screw. The ring includes a split 262 therein for allowing the split ring 258 to be opened during forceful removal from the bone screw. The barrel 254 of the anchor screw 250 and the split ring 258 can be constructed of a malleable material.

With reference to FIG. 19, there is illustrated the manner in which the anchor end 250 is threadably fastened to the threaded end of the wire 252. In addition, the anchor end 250 is shown with a surgical screw 266 inserted through the central opening 260 in the annular split ring 258. As noted above, because the annular ring 258 is formed of a malleable material, it can be deformed, such as upon forceful removal of the anchor end 250 from the surgical screw 266. This is shown in FIG. 20, where the anchor end 250 has been forced in the direction of arrow 268 to thereby remove it from the surgical screw 266 anchored in a bone or other hard material. When forced in the direction of arrow 268, the split ends of the annular ring 258 are forced apart for separation from the shank of the surgical screw 266. The advantage of the split ring is that the anchor screw 266 need not be removed to disengage the anchor end 250 therefrom.

FIG. 21 illustrates a bi-directional bone distraction arrangement similar to that shown in connection with FIG. 16, but equipped with the split ring anchor ends 250 shown in FIGS. 17–20. The first expansion device 270 has threaded wire arms 272. While not shown, those skilled in the art may prefer to also threadably fasten the arms 272 to the respective bases 192 and 196 to provide further adjustment to the effective lengths of the arms. The second expansion device 276 is similarly constructed with threaded arms having the split ring anchor ends 250 threadably attached thereto. The split ring anchor ends 250 of each such expansion device 270 and 276 are fastened to the center surgical screws 278, as shown in FIG. 22. As can be appreciated, the split ring anchor ends 250 can be rotated to the particular orientation desired. The force exerted by the expansion device 270 to effect the removal of the split ring anchor ends from the surgical screw is carried out by turning the adjustment screw in the direction to cause contraction between the parts thereof. In addition, the expansion device 270 can be physically grabbed with pliers or the like to pull the device from engagement with the surgical screws.

FIGS. 23–26 illustrate a procedure in which maxilla repositioning can be achieved by employing the bone distraction device according to the invention. FIG. 23 shows a left view and FIG. 24 shows a right view of the maxilla 300 severed from the other facial bones. An osteotomy 302 is effective to sever the maxilla 300 from the pyriform bone 304, the zygoma bone 306 and the zygomatic arch 308. Also shown is the nasal bone 310 and the orbit 312. Further, the osteotomy 302 extends downwardly to sever the maxilla 300 from the pterygoid bone 314.

A first distraction device 302 spans the osteotomy 302 between a posterior portion of the maxilla 300 where the zygoma bone 306 joins the zygomatic arch 308. The expansion device 320 can be of the type shown in FIG. 4 or one of the devices shown in FIG. 14. The expansion device 320 incudes four crimped anchor ends, of the type having a C-shaped deformable split ring, such as shown in FIGS. 18–20. The adjustment screw of the expansion device 320 is adjustable by way of a flexible handle 322 that is fixed to the device. The flexible handle 322 protrudes through the soft tissue incision of the mucosal flap in the patient's oral cavity and is thus accessible for adjusting the expansion device 320. When the expansion device 320 is adjusted so as to expand, the posterior portion of the maxilla 300 is moved in the direction of arrow 324.

A second expansion device 330 shown in FIG. 24 is fixed on the right-hand severed portion of the maxilla 300 by a first set of anchor screws, and fixed to the zygoma bone portion by a second set of anchor screws. The expansion device 330 is substantially identical to the left-hand expansion device 320 shown in FIG. 23. When adjusted by the flexible handle 332 the posterior portion of the maxilla 300 is lengthened in the direction shown by arrow 334. The sectioning of the maxilla 300 as well as the installation and adjustment of the expansion devices 320 and 330 can all be carried out intra-orally, without making any incisions in the exterior facial tissue of the patient. As can be appreciated, when lengthening the maxilla using the intra-oral expansion devices constructed according to the invention, no external appliances are required, as is the practice of the prior art. The extension or expansion of the maxilla is otherwise known as the modified High LeFort I osteotomy technique.

FIGS. 25 and 26 illustrate the procedure for installing the third expansion device 340 in the oral cavity palatal area of the maxilla. FIG. 25 illustrates in broken line 342, an incision in the palatal mucosal tissue to form a flap 344 that is lifted back. Importantly, the blood vessels 346 and 348 are not disturbed. The maxilla 300 is cut along a rectangular-shaped line 350 in the palatal area of the patient's mouth. The osteotomy 350 results in the maxilla being separated into movable section 300a and stationary section 300b. Shapes other than a cut in a rectangular shape can be effective in lengthening the maxilla 300. Next, the palatal mucosal tissue flap 344 is replaced and the margins of the incision are sutured together.

With reference to FIG. 26, there is shown the third expansion device 340 spanning the maxilla cut 350. In accordance with an important feature of the invention, the expansion device 340 is not buried under the mucosal tissue, but rather is anchored to the severed maxilla using four transmucosal screws, one shown as reference numeral 352. A pair of transmucosal screws 352 fasten the one end of the expansion device 340 to the severed and stationary maxilla portion 300b, and another pair of transmucosal screws fasten the other end of the expansion device 340 to the movable portion 300a of the severed maxilla. Once fixed to the maxilla in the manner shown in FIG. 26, the expansion device 340 can be activated and moved so as to reposition the bone portion 300a in the direction shown by arrow 358. While the adjustment screw 366 is shown extending toward the posterior portion of the oral cavity, the expansion device 340 can be reversed in position, so that the expansion screw 366 faces toward the anterior portion of the patient's oral cavity. In any event, the expansion device 340, being exposed in the oral cavity of the patient, is readily accessible for adjustment by turning the screw 66.

As can be seen from the foregoing, by using three expansion devices in the manner noted above, the maxilla 300 can be moved downward and forward to correct various types of upper jaw deformities. Indeed, the expansion devices can be fixed across the maxilla osteotomy so as to achieve the repositioning of the maxilla 300 in directions different from that described above.

While the present invention has been described above with a certain degree of particularity, it is understood that the present disclosure has been made by way of example, and changes in detail of structure may be made to the invention without departing from the spirit and scope thereof, as defined by the appended claims. Those skilled in the art may prefer to combine the various and different features of the embodiments disclosed, or utilize the individual features and advantages.

What is claimed is:

1. A bone distraction device for applying a uniform expansion pressure to a plurality of anchor posts set into a bone, comprising in combination:

an expansion device having a first part movably attached to a second part and an adjustment mechanism for axially moving said first part with respect to said second part;

anchor post engaging apparatus for connecting said expansion device to an anchor post, each said anchor post engaging apparatus having only two components, including 1) an anchor end, and 2) a rigid arm;

said anchor end being structured for engaging with a respective anchor post and attachment to a distal end of said rigid arm, and said rigid arm having no bends at said distal end when attached to said anchor end, thus reducing any compromise in the transfer of lateral forces; and a proximal end of said rigid arm fastened to said expansion device and said rigid arm constructed so as to be adjustable in length by a surgeon, thereby allowing said anchor end to be spaced a desired distance from said expansion device.

2. The bone distraction device of claim 1, wherein said rigid arm is constructed of a wire.

3. The bone distraction device of claim 1, wherein said rigid arm has threads formed on at least one end thereof, and at least one of said anchor end or said expansion device has threads engageable with the threads of said rigid arm, and said threads are effective to adjust a lateral distance from said anchor end to said expansion device.

4. The bone distraction device of claim 3, wherein said anchor end has a receptacle with a lateral bore for receiving therein an end of said rigid arm.

5. The bone distraction device of claim 4, wherein the receptacle of said anchor end is constructed so as to be crimped to said rigid arm.

6. The bone distraction device of claim 4, wherein said lateral bore has an internal stop formed integral with said receptacle for abutment with an end of said rigid arm.

7. The bone distraction device of claim 3, wherein said anchor end includes a split ring having a central opening for engagement around an anchor post, and being constructed of a deformable material to allow portions of said split ring to separate at a split therein to allow forceful removal thereof from the anchor post.

8. The bone distraction device of claim 1, further including two said rigid arms attached to said first part and two said rigid arms attached to said second part, and at least one said rigid arm of said four rigid arms being shorter than the other three rigid arms prior to attachment thereof to a respective said anchor end.

9. The bone distraction device of claim 1, wherein said bone distraction device is adapted to be fixed to a bone so as to span a distraction gap in the bone, and further including a second said bone distraction device fixed to the bone so as to span a second distraction gap in the bone, said first and second bone distraction devices being anchored to the bone by at least one common screw fixed to the bone.

10. The bone distraction device of claim 1, wherein a distal end of one said rigid arm is formed integral with said anchor end, and a proximal end of said one rigid arm is removably attached to said expansion device.

11. The bone distraction device of claim 1, further including four pairs of said components, each for engaging with a different anchor post.

12. The bone distraction device of claim 1, wherein said anchor post comprises a screw.

13. The bone distraction device of claim 1, wherein said rigid arm is constructed so as to be severed prior to attachment to one of said expansion device or said anchor end, thereby adjusting the spacing between said anchor end and said expansion device.

14. The bone distraction device of claim 1, wherein said rigid arm is structured so as to be adjusted to extend said anchor end away from said expansion device without bending of said rigid arm.

15. A method of constructing a bone distraction device, comprising the steps of:

forming a first part and a second part movable with respect to each other;

forming a first member so as to be attached to said first part and extending therefrom;

forming a second member so as to be attached to said second part and extending therefrom;

forming a respective anchor end for attachment to each said member, and forming said first and second members so as to be adjustable in effective length to thereby vary the spacing between said anchor ends and the respective first and second parts during use of the device; and forming each said anchor end with a portion thereof having an opening for engaging with an anchor post secured within a bone, each said anchor end further being formed with a tubular receptacle formed integral with said portion, and said tubular receptacle having an internal closed end.

16. The method of claim 15, further including fastening said first and second member to said respective first and second parts by a threadable engagement therebetween.

17. The method of claim 15, further including attaching an anchor end to a respective said first or second member by crimping.

18. The method of claim 15, further including attaching an anchor end to a respective said first or second member by threadable engagement.

19. The method of claim 15, further including forming the first and second members adjustable in length by forming threads on at least one end of said members.

20. The method of claim 15, further including forming the first and second members adjustable in length by forming at least one end thereof for clipping off a portion thereof.

21. A method of using a bone distraction device, comprising the steps of:

installing at least two spaced apart bone screws to a severed bone, said bone screws being set in the bone on different sides of a cut in the bone;

adjusting a length of at least one of a plurality of arms attached to a body portion of the bone distraction device;

attaching an end to said adjusted arm for engaging a bone screw;

installing said device for engagement between the bone screws; and adjusting said device to expand a first part from a second part of said device to thereby force the bone screws apart and thereby separate the severed bone.

22. The method of claim 21, further including adjusting the length of said arm by cutting off a portion thereof.

23. The method of claim 21, further including installing the device intra-orally.

24. The method of claim 21, further including removing said bone distraction device without removing all of the bone screws.

25. The method of claim 21, further including selecting one of a plurality of said arms for shortening a length thereof, making the length of the selected arm shorter, and thereafter attaching the bone screw engaging end thereto.

26. The method of claim 21, further including installing at least one of the screws through soft tissue into the severed bone, and attaching one said end to the screw between a head of the screw and the soft tissue.

27. The method of claim 21, wherein the severed bone is a severed mandible.

28. The method of claim 21, wherein the severed bone is a severed maxilla.

29. A bone distraction device, comprising in combination:
an expansion device having two parts that are coupled together with a threaded rod so that when the threaded rod is rotated, the expansion device parts are moved apart in an axial direction;
an anchor end structured for engagement with a post anchored in a bone; and
a plurality of rigid wire arms, at least one end of each wire arm being threaded and engageable with a threaded part in one of said expansion device or said anchor end, whereby rotation of said arms is effective to adjust a spacing of said anchor ends in said axial direction from said expansion device without removing said bone distraction device from a patient.

30. The bone distraction device of claim 29, wherein said anchor end includes a threaded bore and comprises a forked member.

31. The bone distraction device of claim 29, wherein each said arm is threaded at both ends thereof, with right hand threads at one end and left hand threads at an opposite end thereof.

* * * * *